United States Patent
Inoue

(10) Patent No.: US 7,951,075 B2
(45) Date of Patent: May 31, 2011

(54) INSPECTION METHOD WITH ENDOSCOPE

(75) Inventor: Haruhiro Inoue, Yokohama (JP)

(73) Assignees: Olympus Medical Systems Corp., Tokyo (JP); Showa University, Tokyo (JP)

(*) Notice: Subject to any disclaimer, the term of this patent is extended or adjusted under 35 U.S.C. 154(b) by 1069 days.

(21) Appl. No.: 11/788,964

(22) Filed: Apr. 23, 2007

(65) Prior Publication Data

US 2008/0262315 A1  Oct. 23, 2008

(51) Int. Cl.
A61B 1/00 (2006.01)
A61B 1/015 (2006.01)

(52) U.S. Cl. .......... 600/168; 600/156; 600/101

(58) Field of Classification Search .......... 600/168, 600/156, 101, 176, 476, 478, 153, 157, 158, 600/129
See application file for complete search history.

(56) References Cited

U.S. PATENT DOCUMENTS

| 5,014,709 | A  | * | 5/1991 | Bjelkhagen et al. | 600/431 |
| 6,425,535 | B1 |   | 7/2002 | Akiba |  |
| 7,267,648 | B2 | * | 9/2007 | Hasegawa | 600/168 |
| 2003/0153812 | A1 | * | 8/2003 | Hutchison et al. | 600/168 |
| 2003/0163049 | A1 | * | 8/2003 | Balas | 600/476 |
| 2006/0270906 | A1 | * | 11/2006 | Matsuno | 600/156 |
| 2007/0077202 | A1 | * | 4/2007 | Yamamoto et al. | 424/9.1 |
| 2007/0149851 | A1 | * | 6/2007 | Nakamura et al. | 600/129 |
| 2007/0172912 | A1 | * | 7/2007 | Yamamoto et al. | 435/40.5 |
| 2008/0045859 | A1 | * | 2/2008 | Fritsch et al. | 600/567 |
| 2009/0253991 | A1 | * | 10/2009 | Balas et al. | 600/477 |

FOREIGN PATENT DOCUMENTS

| JP | 2005-000640 | 1/2005 |
| JP | 2006-320366 | 11/2006 |

* cited by examiner

Primary Examiner — John P Leubecker
(74) Attorney, Agent, or Firm — Scully, Scott, Murphy & Presser, P.C.

(57) ABSTRACT

An endoscopic inspection method includes staining step and super magnified observation step. In the staining step, a distal end surface of a distal end portion of an endoscope which includes a distal end opening of a channel and a first lens that forms a super high-power observation optical system is held in contact with the tissue surface of the observation subject region such that the staining fluid supplied via the channel penetrates to the gap between the distal end surface and the tissue surface to eliminate the mucus on the tissue surface. The tissue surface having the mucus eliminated is stained with the staining fluid. In the super magnified observation step, the first lens which forms the super high-power observation optical system provided at the distal end portion is brought into contact with the tissue surface that has been stained with the staining fluid such that the observation at the cellular level is performed.

9 Claims, 10 Drawing Sheets

INSPECTION METHOD WITH ENDOSCOPE

BACKGROUND OF THE INVENTION

1. Field of the Invention

The present invention relates to an endoscopic inspection method for diagnosis through observation of the stained tissue with a high-power observation optical system of an endoscope.

2. Description of the Related Art

Recently, Japanese Unexamined Patent Application Publication No. 2005-640 has disclosed an endoscope including, at a distal end portion thereof, an observation subject region contact-type observation optical system for observing an observation subject region in a state where an objective optical system is brought into contact with the observation subject region, in addition to a normal observation optical system for observing the observation subject region in a state where the objective optical system is not brought into contact with the observation subject region.

Japanese Unexamined Patent Application Publication No. 2006-320366 discloses the endoscope equipped with a super high-power image pickup unit including a super high-power lens unit. The power of the super high-power lens unit is equivalent to that of the histological observation level for observing the cell, gland duct structure and the like, that is, the power level is 200 to 1000 times higher than that of the normal optical microscope. The endoscope allows the super high-power magnified observation and the histological observation with respect to the cell and the gland duct structure by bringing the surface of the distal end of the lens unit into contact with the surface of the tissue. The observation subject region is stained through spray of the dye to the interest region before performing the histological observation such that the outline of the cell is clarified to observe the cell nucleus.

U.S. Pat. No. 6,425,535 discloses the endoscope equipped with means for spraying the dye through the channel.

In the observation subject region such as the stomach or the large intestine, there is mucus on the tissue surface. Therefore in the case the dye is sprayed toward the observation subject region through the treatment instrument channel or the auxiliary water feed channel of the endoscope, the penetration of the dye into the observation subject region is disturbed by the mucus. In other words, it is difficult to allow the observation subject region to be stained as required by the operator during the endoscopic observation. It has been difficult to perform the histological observation in addition to the normal observation.

SUMMARY OF THE INVENTION

According to the present invention, an endoscopic inspection method with a high-power observation optical system includes mucus eliminating and staining step for penetrating a staining fluid supplied through a channel into a gap between a distal end surface and a tissue surface to eliminate a mucus on the tissue surface while maintaining the distal end surface of a distal end portion of an endoscope having a distal end opening of the channel and a first lens which forms a super high-power observation optical system in contact with the tissue surface of an observation subject region, and staining the tissue having the mucus eliminated with the staining fluid, and super magnified observation step for performing a magnified observation at a cellular level by bringing the first lens which forms the super high-power observation optical system at the distal end portion into contact with the tissue surface which has been stained with the staining fluid.

The above and other objects, features and advantages of the invention will become more clearly understood from the following description referring to the accompanying drawings.

DETAILED DESCRIPTION OF THE PREFERRED EMBODIMENTS

Figure 1:
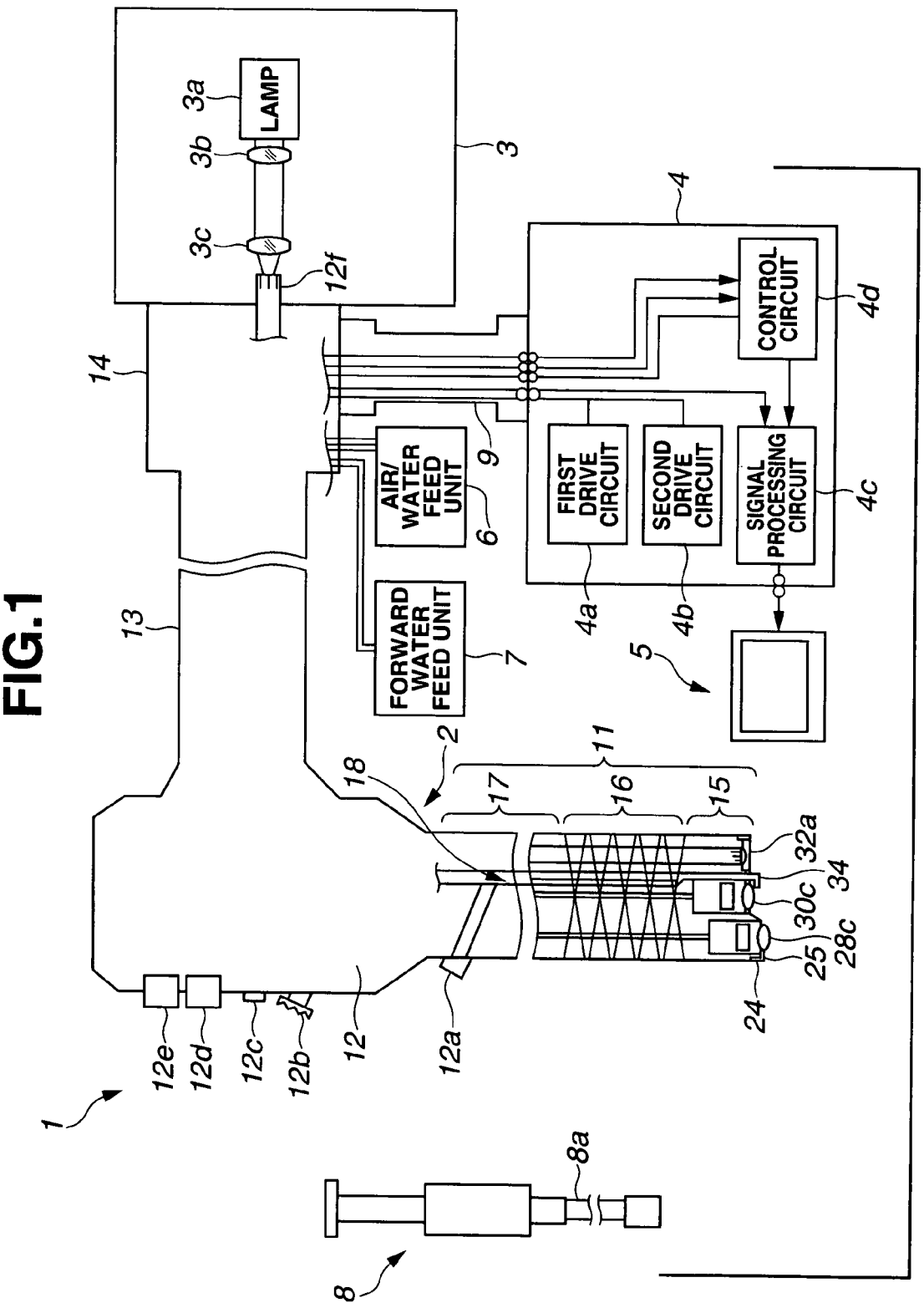
FIG. 1 is an explanatory view showing an entire configuration of the endoscope system.

The embodiment of the present invention will be described referring to the drawings.

An endoscope system 1 is mainly formed of an endoscope 2, a light source device 3, a processor 4, a monitor 5, an air/water feed unit 6, a forward water feed unit 7, and a syringe 8.

The endoscope 2 includes an elongated insertion portion 11 which is inserted into a body cavity. An operation portion 12 is attached to a proximal end of the insertion portion 11. A universal cable 13 extends from the side of the operation portion 12. A connector 14 is attached to an end portion of the universal cable 13 so as to be detachably connected to the light source device 3. A scope cable 9 connected to the processor 4 is detachably connected to the connector 14.

The insertion portion 11 is formed of a rigid distal end portion 15, a bending portion 16, and a flexible pipe 17 that exhibits flexibility, which are connected in the order from the side of the distal end portion. The bending portion 16 is provided with a plurality of bending pieces so as to be bent in the longitudinal and lateral directions.

The operation portion 12 includes a treatment instrument insertion port 12a, a zoom lever 12b, a forward water feed button 12c, control switches 12d, 12e, a not shown bending operation knob, an air/water feed button and the like. The treatment instrument insertion port 12a is communicated with a treatment instrument channel 18 serving as a suction channel. The syringe 8 is detachably connected to the treatment instrument insertion port 12a directly or indirectly via a connection tube 8a. The first control switch 12d is operated by the operator for outputting the command signal to switch the observation mode to the processor 4. The second control switch 12e is operated by the operator for generating the signal for such command as freezing, for example. The bending operation knob is operated by the operator and the like for operating the bending portion 16 in the longitudinal or the lateral direction.

Figure 2:
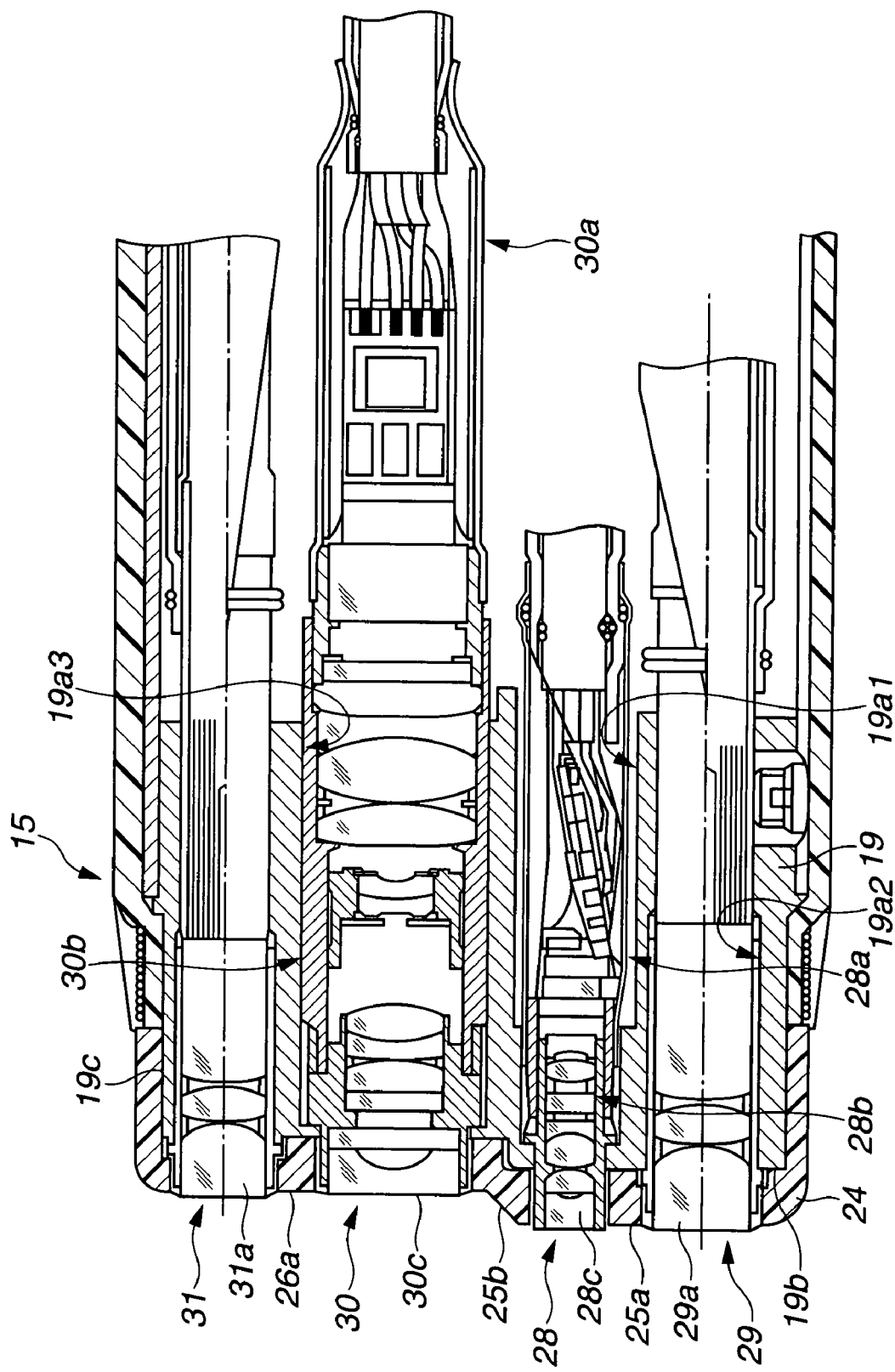
FIG. 2 is a sectional view showing an essential portion within a distal end portion of an insertion portion of the endoscope.

Referring to FIG. 2, a rigid distal end portion 19 formed of a rigid metal such as stainless steel is formed at the distal end portion 15. The rigid distal end portion 19 is provided with a first image pickup unit 28 that forms a super high-power observation optical system, a first illumination unit 29, a second image pickup unit 30 that forms a normal observation optical system, a second illumination unit 31, a third illumination unit 32, a distal end opening 18a of the treatment instrument channel 18, an air/water feed nozzle 34, a forward water feed opening 35a and the like.

The first image pickup unit 28 as a subject contact type includes a super high-power lens unit 28b serving as the super high-power observation optical system, and an image pickup unit 28a equipped with the image pickup device such as CCD and CMOS. The super high-power denotes the magnification at the level for the histological observation with respect to the cell and the gland duct structure, in other words, the magnification corresponding to 200 to 1000 times higher than that of the normal optical microscope, allowing the magnified observation at the cellular level (hereinafter referred to as the super magnified observation).

Meanwhile, the second image pickup unit 30 is used as the observation optical system for performing the normal observation, and includes an image pickup unit 30a equipped with the image pickup device such as CCD and CMOS, and a movable optical unit 30b as a zooming optical system capable of continuously changing the observation magnification from zoom to wide.

The operator operates the control switch 12d disposed on the operation portion 12 to switch the observation mode from normal to super magnified. The endoscope 2 is originally set to be in the normal observation mode upon start of the inspection. The movable optical unit 30b is moved by the operator to operate the zoom lever 12b disposed on the operation portion 12 for zooming. The movable optical unit 30b is driven so as to advance and retract along the optical axis, and is moved forward to be ready for the wide angle observation.

A plurality of holes 19a1, 19a2 and the like are formed in the rigid distal end portion 19. For example, the first hole 19a1 is formed to allow attachment of the component of the first image pickup unit 28. The second hole 19a2 is formed to allow attachment of the component of the first illumination unit 29. The third hole 19a3 is formed to allow attachment of the component of the second image pickup unit 30.

Figure 3:
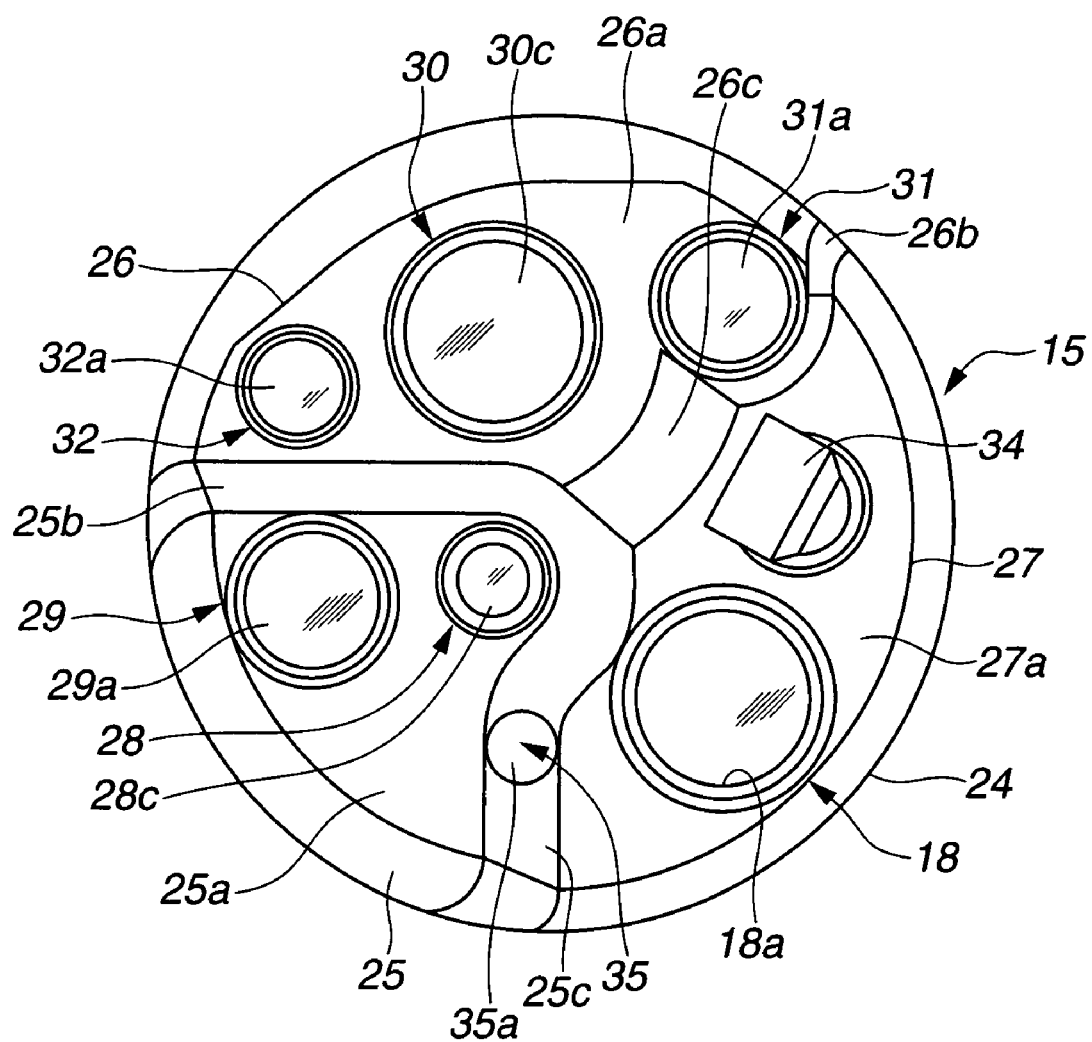
FIG. 3 is a front view of the distal end portion of the insertion portion shown in FIG. 2.

A distal end cover 24 is fit with a distal end surface 19b and an outer peripheral surface 19c of the rigid distal end portion 19 at the distal end side. Three stepped portions including a protruding stepped portion (hereinafter referred to as the protrusion) 25 which protrudes forward, an intermediate stepped portion 26 which is one step lower than the protrusion 25, and a lower stepped portion 27 which is one step lower than the intermediate stepped portion 26 are formed on a distal end surface 15a of the distal end portion 15 with which a distal end cover 24 is fit as shown in FIGS. 2 and 3, for example. The end surface of the protrusion 25 is defined by a plane 25a orthogonal to the longitudinal axis of the insertion portion 11.

A first lens 28c and a first illumination window 29a are provided on the plane 25a of the protrusion 25. The first lens 28c forms the first image pickup unit 28 as the observation lens. The first image pickup unit 28 is placed substantially at the center of the distal end portion 15. The first illumination window 29a is disposed at the outer peripheral side in the vicinity of the first image pickup unit 28.

The intermediate stepped portion 26 includes a plane 26a substantially in parallel with the plane 25a of the protrusion 25. A first lens 30c, a second illumination window 31a, and a third illumination window 32a are formed on the plane 26a of the intermediate stepped portion 26. The first lens 30c forms the second image pickup unit 30 as the observation lens. The illumination windows 31a, 32a are formed at both sides of the second image pickup unit 30.

The difference in the level between the plane 25a of the protrusion 25 and the plane 26a of the intermediate stepped portion 26 is set to approximately 0.7 mm enough to prevent the protrusion 25 from being in the visual field of the second image pickup unit 30. An inclined surface 25b inclined at about 45° is formed on the wall between the intermediate stepped portion 26 and the protrusion 25.

The lower stepped portion 27 includes a plane 27a substantially in parallel with the plane 25a of the protrusion 25. A distal end opening 18a of the treatment instrument channel 18, and the air/water feed nozzle 34 are formed on the plane 27a of the lower stepped portion 27. An inclined surface 26b inclined at about 45° and a fluid guide surface 26c inclined at the angle smaller than that of the inclined surface 26b are formed on the wall between the lower stepped portion 27 and the intermediate stepped portion 26. The fluid guide surface 26c is formed between the air/water feed nozzle 34 of the lower stepped portion 27 and the second image pickup unit 30 of the intermediate stepped portion 26. The fluid guide surface 26c is defined by the gently inclined surface at the inclined angle of about 18°.

An inclined surface 25c inclined at about 45° is formed on the wall between the lower stepped portion 27 and the protrusion 25. An opening 35a of a conduit 35 for the forward water feed is formed in the inclined surface 25c.

In the embodiment, among three illumination windows 29a, 31a and 32a formed on the distal end surface 15a, the first illumination window 29a has the largest area, and the second illumination window 31a has the second largest area. The third illumination window 32a has the smallest area. Among those three illumination windows 29a, 31a and 32a, the intensity of light irradiated from the first illumination window 29a is set to be the highest, the intensity of light irradiated from the third illumination window 32a is set to be the lowest.

In the embodiment, a diameter of the first lens 30c disposed at the distal end of the second image pickup unit 30 is set to be larger than that of the first lens 28c disposed at the distal end of the first image pickup unit 28 for the super magnified observation.

In the embodiment, the light source device 3 includes a lamp 3a and a plurality of lens systems 3b and 3c. The illuminating light passing through the lens system 3c is condensed on the end surface of a light guide 12f. The light source device 3 exhibits the dimming control function (not shown) for adjusting the luminance of the illuminating light. The processor 4 includes a first drive circuit 4a which drives the image pickup device of the first image pickup unit 28, a second drive circuit 4b which drives the image pickup device of the second image pickup unit 30, a signal processing circuit 4c which processes the image pickup signal outputted from the two image pickup devices via the relay substrate (not shown), respectively, and a control circuit 4d which controls the operation state of the aforementioned signal processing circuit 4c.

The procedure for inspection performed with the endoscope 2 in the endoscope system 1 according to the embodiment will be described.

The operator configures the endoscope system 1 for performing the endoscopic observation. More specifically, the operator connects the connector 14 of the endoscope 2 equipped with the first image pickup unit 28 as the super high-power observation optical system to the light source device 3, and connects one end of the scope cable 9 to the connector 14 and the other end of the scope cable 9 to the processor 4. The endoscope 2 is further connected to the air/water feed unit 6 and the forward water feed unit 7, respectively. The syringe 8 which contains the staining fluid such as methylene blue solution is directly or indirectly connected to the treatment instrument insertion port 12a via the connector tube 8a.

The operator turns power switches of the light source device 3, the processor 4 and the like ON so as to be set to predetermined operation states. At this time, the endoscope 2 is set to the observation mode to perform the observation with the second image pickup unit 30, that is, the normal observation mode.

The inspection performed by the operator will be described.

Figure 4:
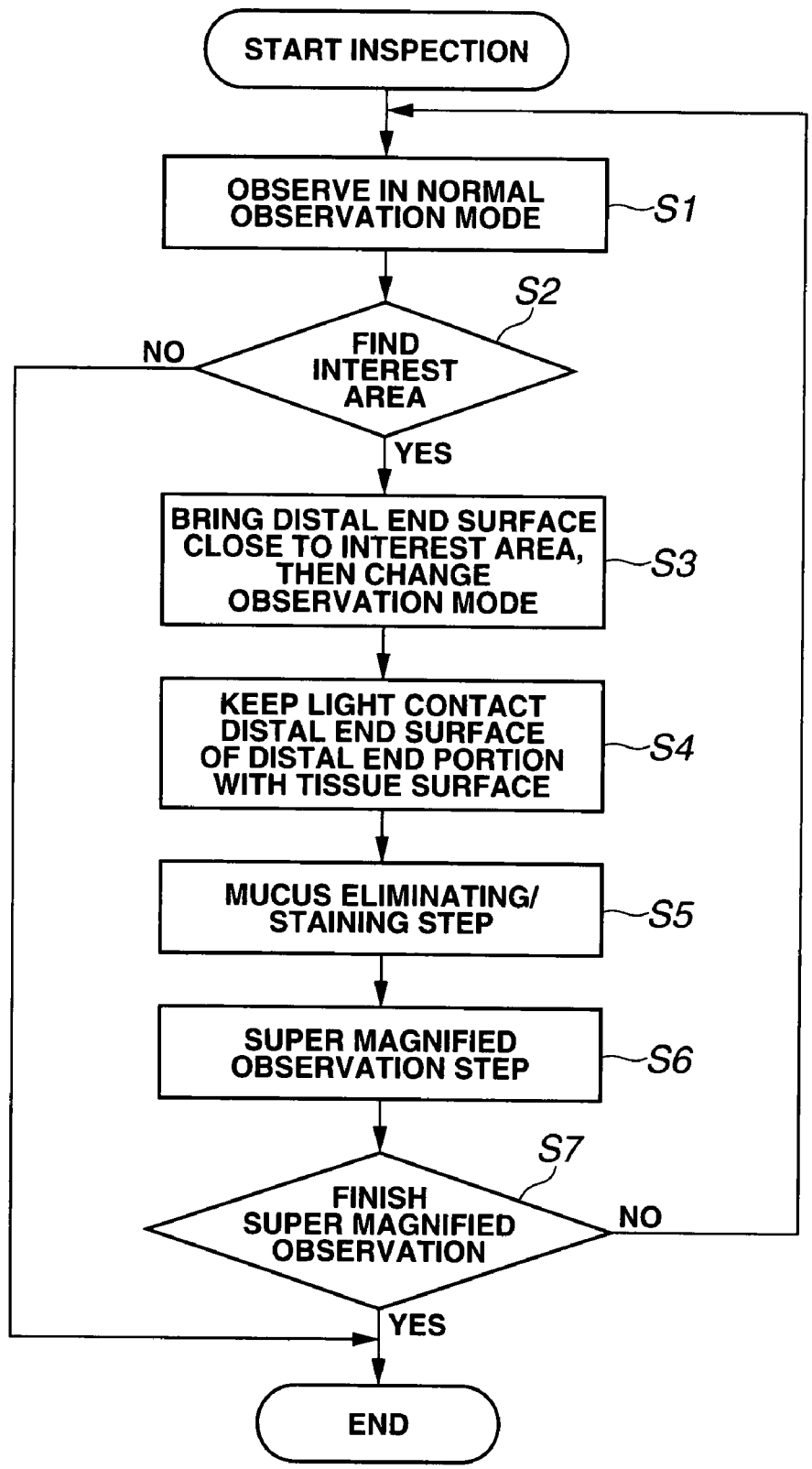
FIG. 4 is a flowchart showing an inspection step performed with the endoscope equipped with a super high-power observation optical system.
Figure 5:
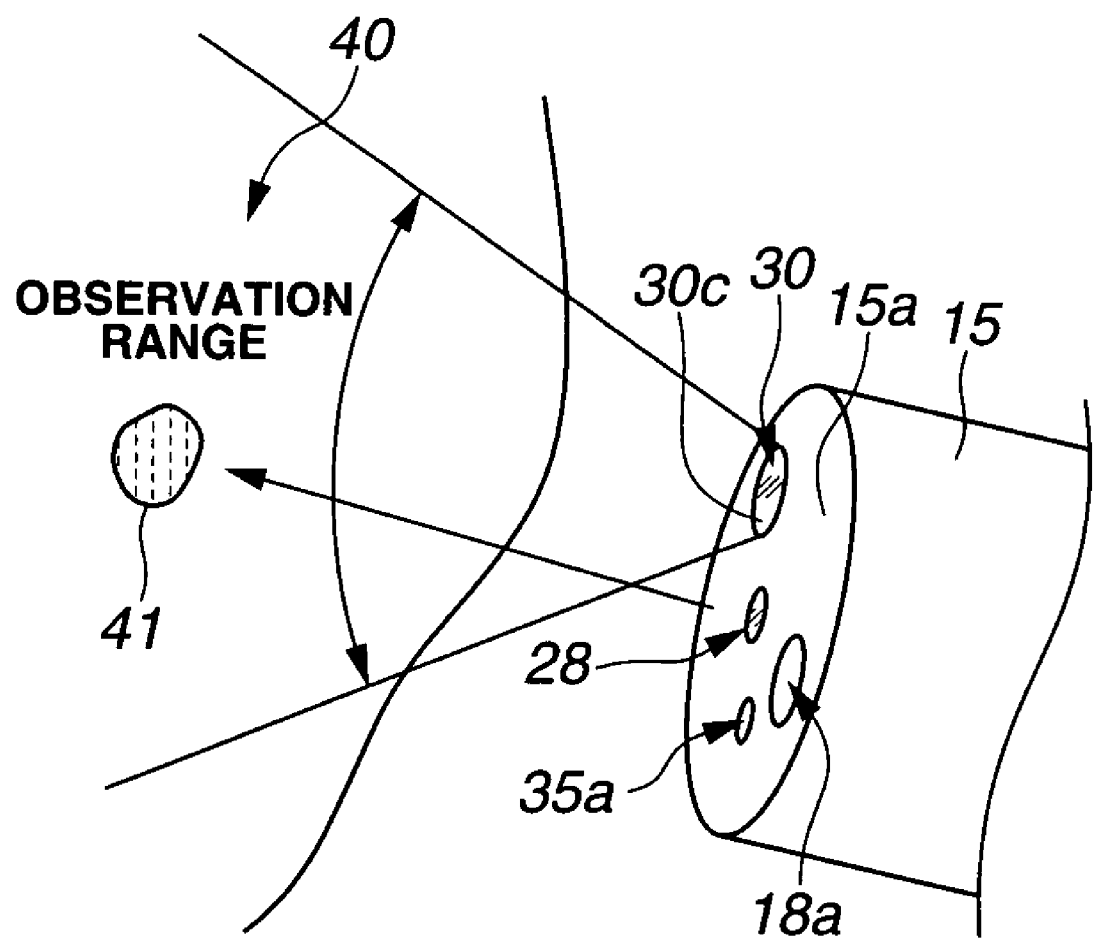
FIG. 5 is an explanatory view showing an observation state in a normal observation mode of the endoscope.

In the normal observation mode as shown in step S1 of FIG. 4, the operator inserts the insertion portion 11 of the endoscope 2 into the body cavity, for example, stomach such that an observation subject region (hereinafter referred to as the observation region) 40 remote from the first lens 30c as shown in FIG. 5 is observed in the wide range with the second image pickup unit 30. The operator performs the observation while performing the magnified observation by operating the zoom lever 12b as needed. The optical image formed on the light receiving surface of the image pickup device of the image pickup apparatus 30a of the second image pickup unit 30 is subjected to photoelectric conversion into the image signal so as to be transmitted to the processor 4. The image signal transmitted to the processor 4 is subjected to the signal processing and outputted to the monitor 5. The endoscope image of the observation subject region picked up by the second image pickup unit 30 is displayed on the screen of the monitor 5.

In step S2, if the operator recognizes an interest area 41 having abnormality in the color and the polyp-like recess or protrusion in the normal observation mode, the process proceeds to step S3.

In step S3, the operator operates the bending knob, pushes the insertion portion 11, performs twisting operation or the like to bring the first lens 28c of the first image pickup unit 28 attached to the distal end surface 15a to be close to the observation region 40 including an interest area 41 as indicated by the arrow in the drawing. If the operator determines that the required approaching state is established based on the screen of the monitor 5, the operator changes the observation mode from the normal observation to the super magnified observation. That is, the operator switches the observation mode of the endoscope 2 to the super magnified observation mode by turning the control switch 12d ON.

Figure 6:
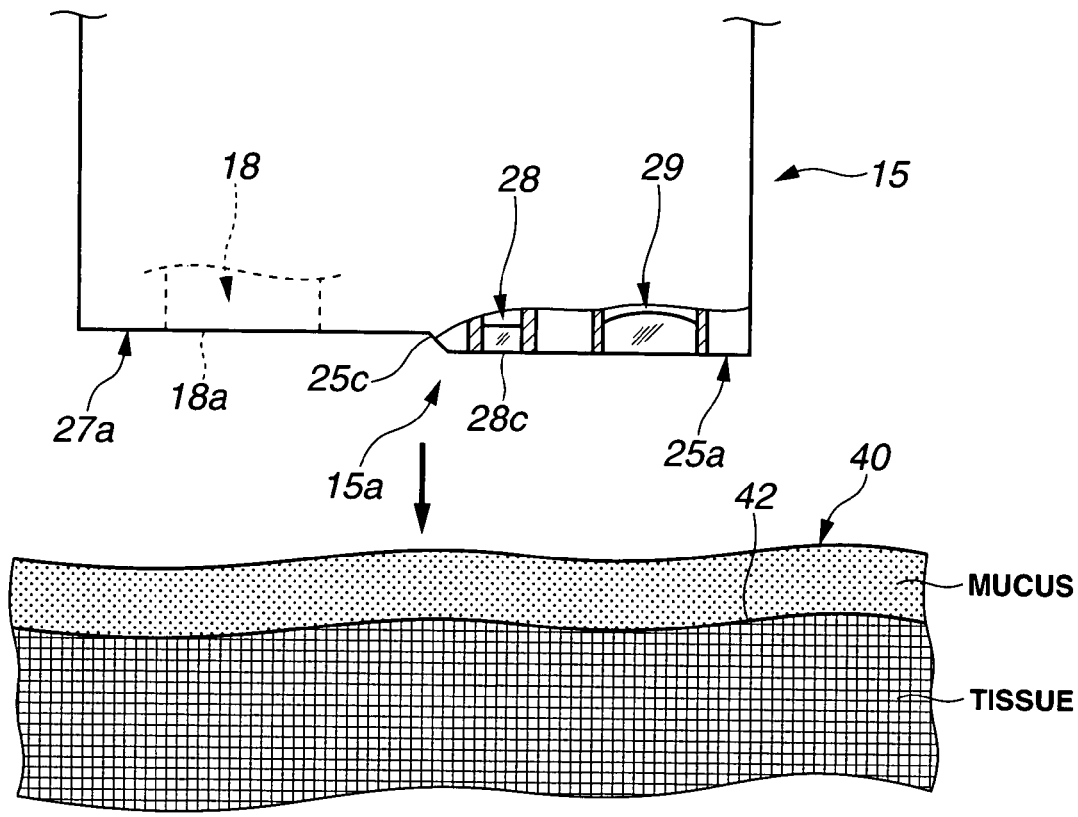
FIG. 6 is an explanatory view showing a state where the distal end portion of the endoscope is closely in contact with the observation subject region in the super magnified observation mode.

Thereafter, the operator brings the first lens 28c of the first image pickup unit 28 attached to the distal end surface 15a to be close to the tissue surface of the observation region 40 in the super magnified observation mode as indicated by the arrow of FIG. 6. If the operator determines that the distal end surface 15a has been in contact with a tissue surface 42 of the observation region 40 based on the operation feel, the process proceeds to step S4.

Figure 7:
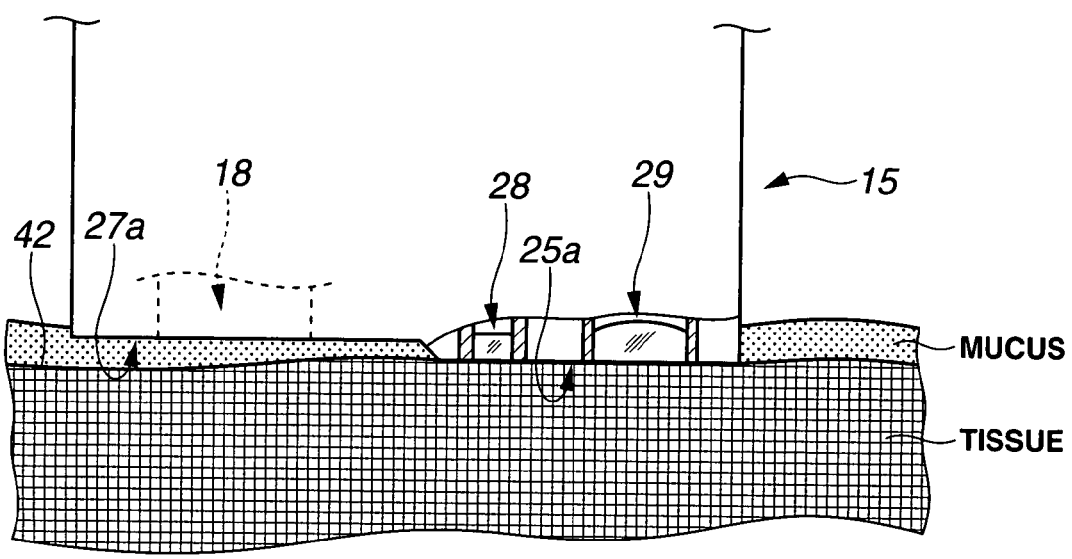
FIG. 7 is an explanatory view showing a state where the surface of the distal end portion is slightly lifted from the tissue surface of the observation subject region.

In step S4, the operator performs the manual operation such that the plane 25a is brought into light contact with the tissue surface as shown in FIG. 7. Then the process proceeds to step S5 for performing mucus eliminating/staining step.

Figure 8:
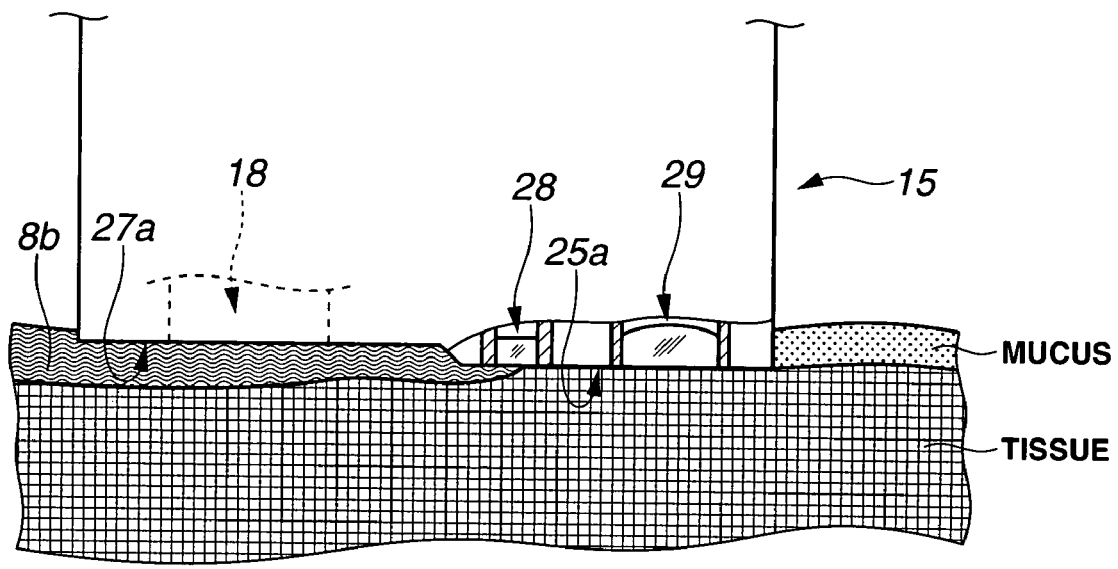
FIG. 8 is an explanatory view showing a state where the staining fluid is supplied through the treatment instrument channel to stain the tissue surface of the observation subject region while eliminating the mucus thereon.

In step S5 for performing the mucus eliminating/staining step, the operator operates the syringe 8 such that the staining fluid contained therein is discharged from the distal end opening 18a through the treatment instrument channel 18. At this time, the plane 27a having the distal end opening 18a is substantially in contact with the tissue surface 42 covered with the mucus. However, the staining fluid 8b discharged from the distal end opening 18a forms the gap between the plane 27a and the tissue surface 42. The staining fluid 8b gradually penetrates into the gap. Thereafter, the staining fluid 8b gradually penetrates the gap between the plane 25a and the tissue surface 42 as shown in FIG. 8 so as to eliminate the mucus and stain the tissue surface 42 having the mucus eliminated.

Figure 9:
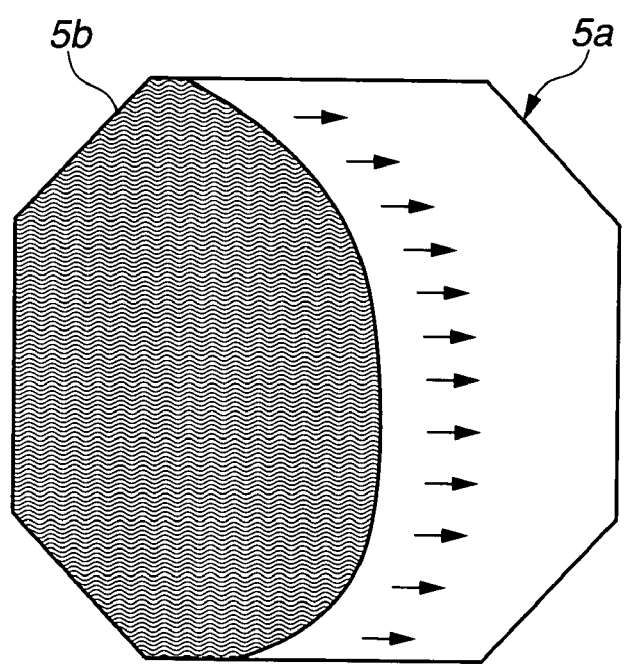
FIG. 9 is a view showing an example of an endoscope image on the monitor screen displaying that the tissue surface is stained with the staining fluid while eliminating the mucus.

At this time, the screen 5a of the monitor 5 displays the image 5b which shows that the staining fluid 8b penetrating into the gap between the distal end surface 15a and the tissue surface 42 has been gradually spread as indicated by the arrow in FIG. 9. The operator continues to operate the syringe 8 while maintaining the light contact between the plane 25a and the tissue surface. The observation region 40 including the interest area 41, that is, the substantially the front surface of the distal end surface 15a substantially in contact with the tissue surface 42 is stained by the staining fluid 8b.

Figure 10:
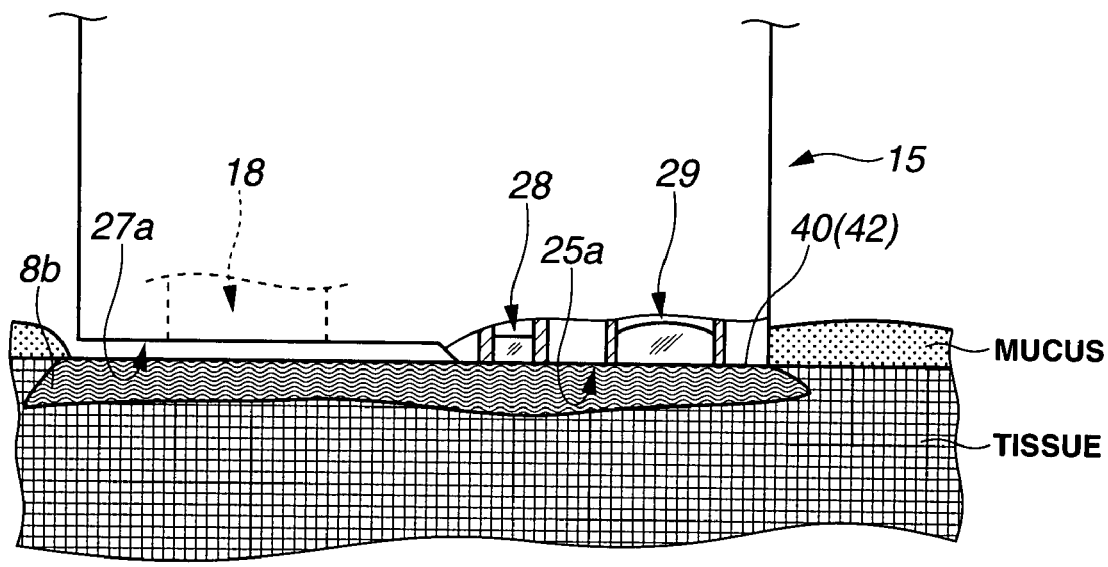
FIG. 10 is an explanatory view showing the state where the super magnified observation is performed with the super high-power observation optical system.
Figure 11:
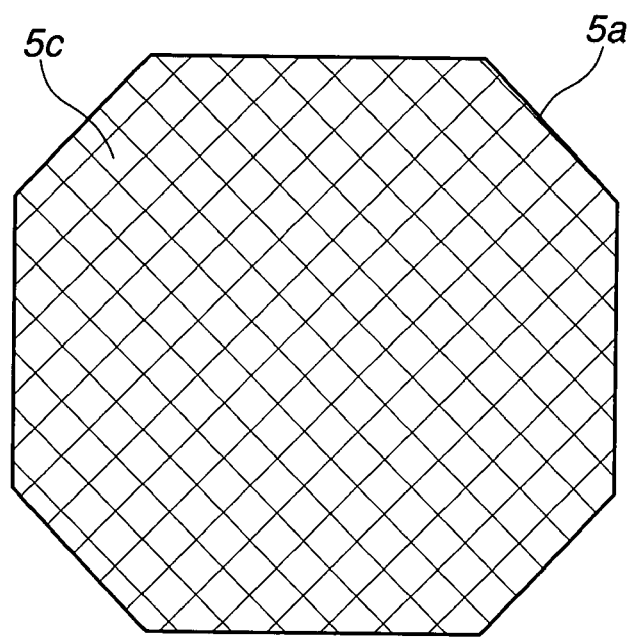
FIG. 11 is a view showing an example of the super magnified observation image displayed on the monitor screen.

If the operator determines that the staining has been finished in the appropriate condition based on the image 5b displayed on the screen 5a of the monitor 5, the process proceeds to step S6 for performing the super magnified observation. In the step, the operator stops supply of the staining fluid, and brings the plane 25a which forms the distal end surface 15a into contact with the observation region 40 including the stained interest area 41 as shown in FIG. 10. As the first lens 28c of the first image pickup unit 28 and the first illumination window 29a formed on the plane 25a contact with the stained tissue surface 42, the optical image of the tissue subjected to the nuclear staining is formed on the light receiving surface of the image pickup device of the image pickup apparatus 28a of the first image pickup unit 28. The image is further subjected to the photoelectric conversion so as to be transmitted to the processor 4. The image signal transmitted to the processor 4 is processed to be outputted to the monitor 5. The super magnified observation image 5c picked up by the first image pickup unit 28 is displayed on the screen of the monitor 5 as shown in FIG. 11. The operator, thus, is allowed to perform the histological observation while viewing the super magnified observation image 5c.

The operator then gradually moves the position of the first lens 28c manually to perform the super magnified observation within the stained observation region 40. The operator is allowed to determine with respect to the state of the cell or the gland duct structure in the interest area 41 based on the super magnified observation.

After the end of the super magnified observation step with respect to the stained interest area with the dye, the operator determines whether or not the super magnified observation is finished in step S7. If the operator decides to continue the super magnified observation in step S7, the control switch 12d is operated to switch the mode from the super magnified observation mode to the normal observation mode, and the process returns to step S1. Meanwhile, if the operator decides to finish the super magnified observation, the control switch 12d is operated to switch the mode from the super magnified observation mode to the normal observation mode, and the insertion portion 11 is pulled out of the body cavity.

If the interest area is not recognized in the normal observation mode in step S1, the operator determines that there is no abnormality, and pulls the insertion portion 11 out of the body cavity.

With the endoscope having the first lens of the image pickup unit as the super high-power observation optical system and the distal end opening of the treatment instrument channel on the distal end surface, the distal end surface is kept in light contact with the tissue surface of the observation subject region to supply the staining fluid onto the tissue surface through the distal end opening. Accordingly, the mucus which covers the tissue surface is eliminated by the staining fluid so as to penetrate into the tissue which has been eliminated by the staining fluid to realize good staining state.

Upon detection of the interest area during the endoscopic observation, the histological observation is performed while staining the portion around the interest area in the state desired by the operator. Accordingly, this may allow determination of the treatment policy without performing the biopsy.

In step S5 for performing the mucus eliminating/staining step, in the case where the distal end surface 15a is in tight fit with the tissue surface to substantially seal the distal end opening 18a, it is difficult to penetrate the staining fluid 8b into the gap between the distal end surface 15a and the tissue surface 42. The image 5b showing that the staining fluid 8b gradually spreads is not displayed on the screen 5a of the monitor 5 as shown in FIG. 9. In the aforementioned case, the operator determines that the distal end surface 15a is in too tight fit with the tissue surface 42, and manually operates such that the distal end surface 15a is in light contact with the plane 25a.

In the aforementioned embodiment, the first lens 28c is formed on the plane 25a, and the distal end opening 18a is formed in the stepped plane 27a. However, the first lens 28c and the distal end opening 18a may be formed on the same plane.

In the aforementioned embodiment, the staining fluid is supplied through the treatment instrument channel 18. However, the channel through which the staining fluid is supplied is not limited to the treatment instrument channel 18. The staining fluid may be supplied through the auxiliary water feed conduit, for example, the forward water feed conduit 35 and the like.

In the aforementioned embodiment, the endoscope is equipped with the image pickup unit for the normal observation and the image pickup unit for the super magnified observation. The endoscope may be configured to include the lens unit which covers the range from the normal observation to the cellular level observation, that is, the super magnified observation.

In the aforementioned embodiment, the endoscope is equipped with the image pickup unit for the normal observation and the image pickup unit for the super magnified observation. The endoscope may be configured such that the observation probe for the super magnified observation is inserted into the treatment instrument channel to supply the staining fluid through the forward water feed conduit.

Figure 12:
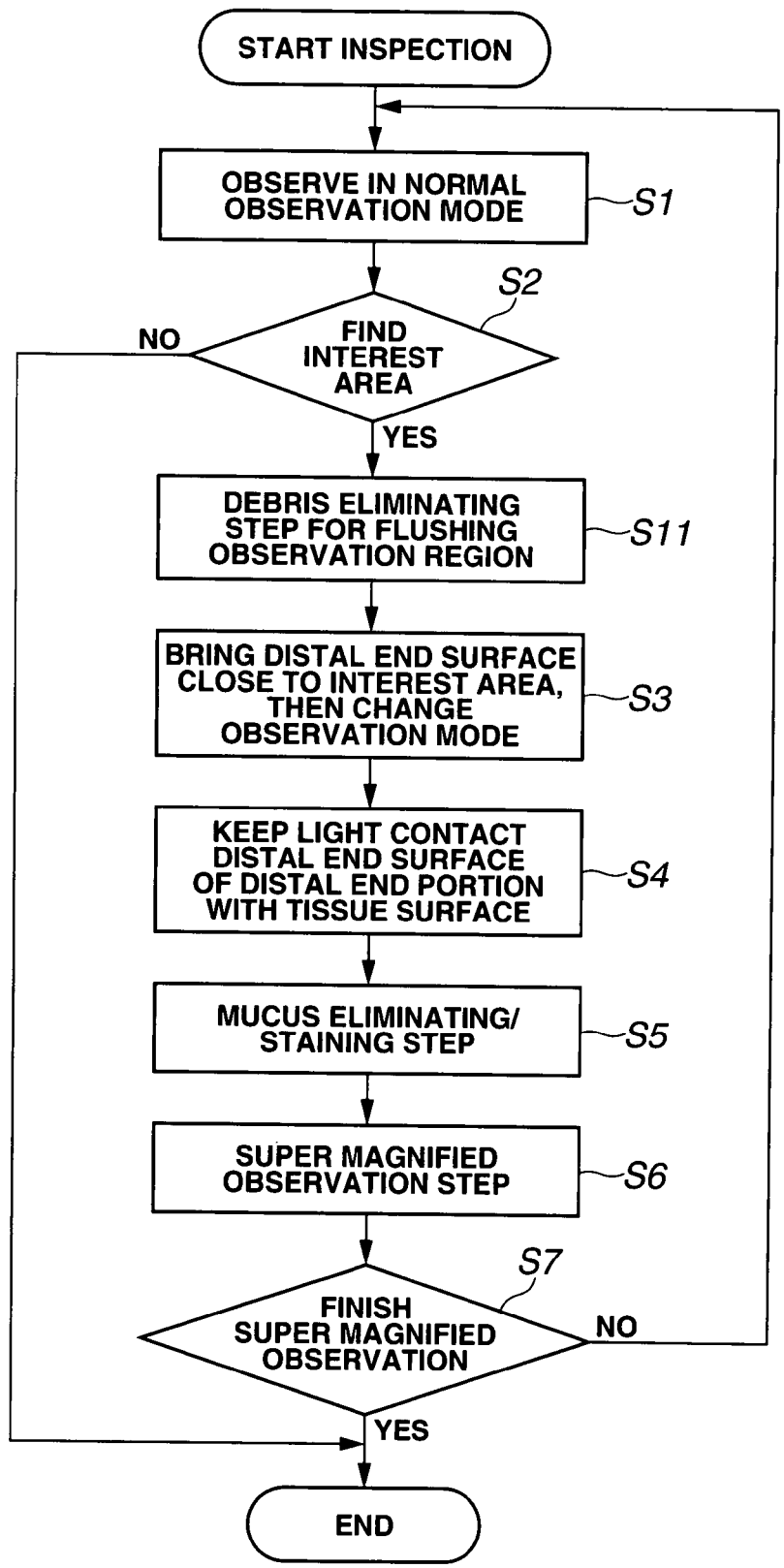
FIG. 12 is a flowchart showing the routine of another inspection step performed by the endoscope equipped with the super high-power observation optical system.

In the aforementioned embodiment, the staining fluid is supplied to perform staining while eliminating the mucus. Alternatively, the observation region 40 may be flushed with water as shown in step S11 before changing the observation mode in step S3 as shown in the flowchart of FIG. 12. Specifically, the normal saline solution is sprayed from the opening 35a of the forward water feed conduit 35 to the observation region 40 to perform the debris eliminating step where the debris adhered to the observation region 40 is removed.

Figure 13:
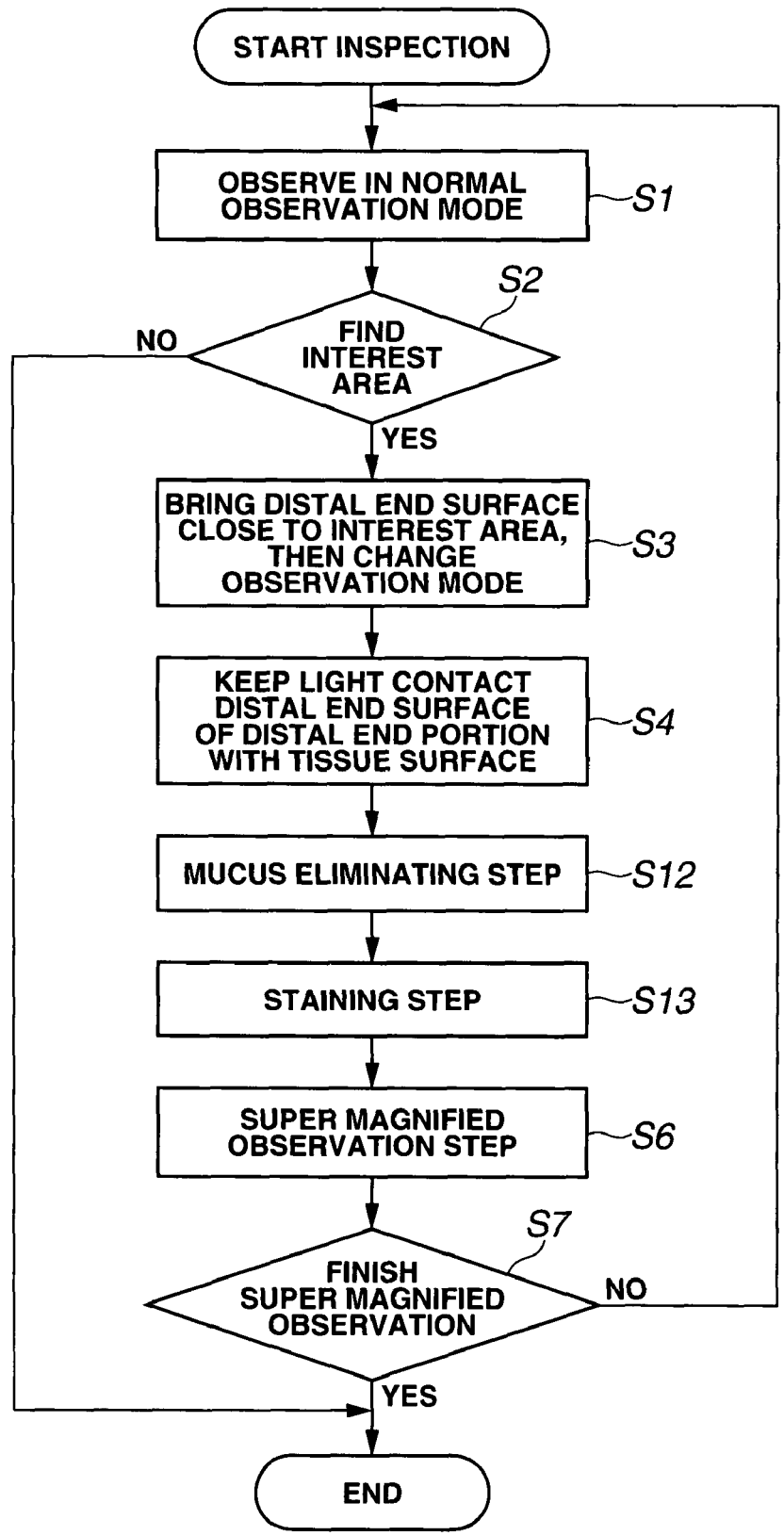
FIG. 13 is a flowchart showing the routine of still another inspection step performed by the endoscope equipped with the super high-power observation optical system.

Referring to the flowchart shown in FIG. 13, the mucus eliminating/staining step in step S5 may be divided into the mucus eliminating step in step S12 and the staining step in step S13. In the aforementioned case, it is required to prepare two syringes for the mucus eliminating and staining. In the mucus eliminating step in step S12, the normal saline solution is supplied from the distal end opening to eliminate the mucus while maintaining the distal end surface 15a in substantially contact with the tissue surface 42. Thereafter, the staining fluid is supplied through the distal end opening to perform the staining. In the mucus eliminating step in step S12, the mucus solubilizer, for example, pronase may be supplied instead of the normal saline solution so as to improve the staining performance.

Having described the preferred embodiments of the invention referring to the accompanying drawings. It should be understood that the present invention is not limited to those precise embodiments and various changes and modifications thereof could be made by one skilled in the art without departing from the spirit or scope of the invention as defined in the appended claims.

What is claimed is:

1. An endoscopic inspection method with a high-power observation optical system comprising:

mucus eliminating and staining step for penetrating a staining fluid supplied through a channel into a gap between a distal end surface and a tissue surface to eliminate a mucus on the tissue surface while maintaining the distal end surface of a distal end portion of an endoscope having a distal end opening of the channel and a first lens which forms a super high-power observation optical system in contact with the tissue surface of an observation subject region, and staining the tissue having the mucus eliminated with the staining fluid; and super magnified observation step for performing a magnified observation at a cellular level by bringing the first lens which forms the super high-power observation optical system at the distal end portion into contact with the tissue surface which has been stained with the staining fluid.

2. The endoscopic inspection method according to claim 1, further comprising step for contacting the distal end surface of the distal end portion with the tissue surface of the observation subject region before performing the mucus eliminating and staining step, and bringing the first lens which forms at least the super high-power observation optical system on the distal end surface in contact with the tissue surface into light contact with the tissue surface.

3. The endoscopic inspection method according to claim 2, wherein when the first lens is lightly in contact with the tissue surface, a determination whether the staining fluid is supplied through the channel is allowed to be made based on the super magnified observation with the super high-power observation optical system.

4. The endoscopic inspection method according to claim 2, further comprising debris eliminating step for eliminating a debris adhered to the observation subject region before contacting the distal end surface of the distal end portion with the tissue surface.

5. The endoscopic inspection method according to claim 1, further comprising step for allowing an observation optical system attached to the distal end portion for performing a normal observation to observe the observation subject region before performing the mucus eliminating and staining step.

6. The endoscopic inspection method according to claim 1, wherein the mucus eliminating and staining step is divided into two steps including:

mucus eliminating step for eliminating the mucus on the tissue surface by water or a mucus solubilizer supplied via the channel; and staining step for penetrating the staining fluid supplied through the channel so as to penetrate to the tissue surface where the mucus has been eliminated.

7. An endoscopic inspection method comprising:

step for observing an observation subject region with an observation optical system provided at a distal end surface of a distal end portion which forms an endoscope for performing a normal observation;

step for contacting the distal end surface with a tissue surface of the observation subject region including an interest area, and lightly contacting a first lens which forms the super high-power observation optical system provided on the distal end surface of the distal end portion which forms the endoscope with the tissue surface while keeping the distal end surface lifted above the tissue surface when the interest area is recognized in the previous step;

mucus eliminating and staining step for eliminating a mucus on the tissue surface with a staining fluid supplied from a distal end opening of a channel formed in the distal end surface of the distal end portion which forms the endoscope, and penetrating the staining fluid to the tissue having the mucus eliminated so as to be stained while keeping at least the first lens in light contact with the tissue surface; and super magnified observation step for performing a magnified observation at a cellular level by contacting the first lens which forms the super high-power observation optical system with the tissue surface stained with the staining fluid.

8. The endoscopic inspection method according to claim 7, further comprising debris eliminating step for eliminating a debris adhered to the observation subject region before contacting the distal end surface of the distal end portion with the tissue surface.

9. The endoscopic inspection method according to claim 7, wherein the mucus eliminating and staining step is divided into two steps including:

mucus eliminating step for eliminating the mucus on the tissue surface by water or a mucus solubilizer supplied via the channel; and staining step for penetrating the staining fluid supplied through the channel so as to penetrate to the tissue surface where the mucus has been eliminated.

* * * * *